United States Patent
Torimae et al.

(10) Patent No.: US 6,218,593 B1
(45) Date of Patent: *Apr. 17, 2001

(54) ABSORBENT ARTICLE

(75) Inventors: Yasuhiro Torimae, Wakayama; Tetsuya Masuki, Tochigi; Tetsuji Kitoh, Wakayama; Jun Sasaki; Manabu Kaneda, both of Tochigi, all of (JP)

(73) Assignee: Kao Corporation, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/817,299
(22) PCT Filed: Oct. 21, 1996
(86) PCT No.: PCT/JP96/03048
    § 371 Date: Apr. 15, 1997
    § 102(e) Date: Apr. 15, 1997
(87) PCT Pub. No.: WO97/15262
    PCT Pub. Date: May 1, 1997

(30) Foreign Application Priority Data

Oct. 27, 1995 (JP) .................................... 7-280948

(51) Int. Cl.$^7$ ........................................ A61F 13/15
(52) U.S. Cl. .................. 604/366; 604/365; 604/370; 604/372; 604/385.31; 604/391
(58) Field of Search ................... 604/365, 366, 604/372, 384, 385.2, 386, 391, 385.24–385.31, 370; 24/442–452

(56) References Cited

U.S. PATENT DOCUMENTS

| | | | |
|---|---|---|---|
| 4,695,278 | * 9/1987 | Lawson | 604/385.2 |
| 5,326,612 | * 7/1994 | Goulait | 24/450 |
| 5,382,400 | * 1/1995 | Pike et al. | |
| 5,595,567 | * 1/1997 | King et al. | 604/391 |
| 5,614,281 | * 3/1997 | Jackson et al. | 604/391 |
| 5,616,394 | * 4/1997 | Gorman et al. | 24/448 |
| 5,624,427 | * 4/1997 | Bergman et al. | 24/442 |
| 5,647,864 | * 7/1997 | Allen et al. | 604/391 |
| 5,669,900 | * 9/1997 | Bullwinkel et al. | 604/391 |
| 5,735,840 | * 4/1998 | Kline et al. | 604/391 |
| 5,762,645 | * 6/1998 | Peck et al. | 604/391 |
| 5,763,041 | * 6/1998 | Leak et al. | 24/447 |

* cited by examiner

Primary Examiner—John G. Weiss
Assistant Examiner—K. M. Reichle
(74) Attorney, Agent, or Firm—Birch, Stewart, Kolasch & Birch, LLP

(57) ABSTRACT

An absorbent article includes a liquid permeable topsheet, a liquid impermeable back sheet, and an absorbent member interposed between the topsheet and the back sheet. While worn, the absorbent article forms a front waist body portion located at the front waist of a wearer and a rear waist body portion located at the rear waist of a wearer. The rear waist body portion has at each side thereof a fastening member for fastening the absorbent article, wherein the back sheet is made up of laminated sheeting composed of a finely porous resin film and nonwoven fabric. The fastening member is formed of a male sheet member of a mechanical fastener and designed to be brought into direct contact with the surface of the nonwoven fabric constituting the back sheet. The above-mentioned absorbent article has a good fit on a wearer, exhibits excellent leakproofness and breathability while worn, and has an excellent texture.

7 Claims, 8 Drawing Sheets

ABSORBENT ARTICLE

TECHNICAL FIELD

This invention relates to a disposable absorbent article. More particularly, it relates to a disposable absorbent article, such as diapers for babies and incontinence pads of underwear for adults, which has a good fit on a wearer and exhibits breathability and a soft texture.

BACKGROUND ART

Disposable absorbent articles, such as diapers for babies and underwear for adults, are prevalent in the marketplace. Disposable absorbent articles have been gradually and steadily taking the place of reusable diapers made of cloth. Such absorbent articles typically comprise a liquid permeable topsheet, liquid impermeable back sheet, and an absorbent member interposed between the topsheet and the back sheet, each structure having a substantially rectangular shape. When worn, these structures form a front waist body portion located at the front waist of a wearer, and a rear waist body portion located at the rear waist of a wearer, where the rear waist body portion has at each side thereof a fastening member for fastening the absorbent article.

The above-described absorbent articles are particularly required to have satisfactory performance in leakproofness, breathability, and texture.

The absorbent articles are required to have an improved fastening function to provide improved leakproofness, and a number of proposals concerning this aspect have been made.

In particular, it is necessary that an absorbent article once worn be unfolded and then re-fastened so that any change of the absorbent member during use (whether the absorbent member is in a correct position or whether the absorbent member still has room for absorbing the body liquid, and the like) may be checked to confirm excretion. To this effect, improvement in the fastening function thereof has been demanded.

A fastening system adopted in conventional absorbent articles is comprised of a fastening member formed of an adhesive tape with an adhesive, where the fastening member is stuck to a landing member provided for reinforcement on the surface of the back sheet.

The problem of the conventional disposable diapers having such a fastening system is that, to ensure fastening (to prevent the fastening member from releasing during use) there is accompanied an increased difficulty in unfastening and re-fastening. In order to ensure fastening and yet allow unfastening followed by re-fastening, the landing member should have increased strength and, accordingly, the back sheet should also have increased strength, which makes the back sheet harder and rougher which in turn deteriorates the texture or the fit of the diaper when put on a wearer.

The size of the landing member to be provided on the back sheet is minimized because too large a landing member would give a poor fit. Also, such a large landing member would increase cost. If the landing member is too small, on the other hand, the adhesive tape is liable to be stuck to the surface of the back sheet where no landing member is provided due to a mistake during placement. This being the case, the back sheet will be broken when the adhesive tape is stripped off for re-fastening or when movement of a wearer imposes stress to the adhesive tape.

While an absorbent article is worn by a baby or even an adult, waste liquid excreted from the body (and held in the absorbent member) and body fluid evaporated from the skin covered with the absorbent article make the inside of the absorbent article stuffy, which facilitates diaper rash on the wearer. This is because "breathability" is required of an absorbent article.

To meet the above-described demands, various proposals on films (or sheets) useful as a back sheet have been made to date.

For example, Japanese Patent Publication No. 38011/93 discloses a finely porous sheet obtained by melt-kneading a specific crystalline polymer (e.g., polypropylene) and a specific compound (e.g., a mineral oil), causing phase separation while sheeting (cooling), and stretching the resulting sheet.

However, the finely porous sheet proposed is inferior in leakproofness, especially against low-surface tension liquids, such as urine.

Japanese Patent Laid-Open No. 47031/90 proposes a finely porous film obtained by melt-extruding a crystalline resin, cooling the extruded film under a pressure roll, and subjecting the film successively to heat treatment, stretching, and heat treatment. Japanese Patent Laid-Open No. 75151/90 proposes a finely porous film obtained by molding a crystalline polyproplyene resin into film under specific conditions and stretching the resulting film under specific conditions. Further, Japanese Patent Laid-Open No. 331306/93 proposes a porous film consisting essentially of polypropylene and polyethylene.

Although the films according to these proposals are all excellent at preventing leakage of low-surface tension liquids such as urine, they not only have poor tensile and tear strength but they have a rough texture and are not therefore applicable as a back sheet of absorbent articles.

"Texture" is an attribute required because the skin of babies is soft and sensitive to a little pressure or a sliding action. As above stated, a special reinforcement should be provided on the surface of the back sheet for allowing unfastening followed by re-fastening to check excretion, which results in poor texture. Under the present situation, therefore, no absorbent article that satisfies the requirements of leakproofness and breathability as well as texture has been proposed as yet.

In short, absorbent articles such as disposable diapers are required to be excellent in leakproofness, breathability, and texture. To satisfy these requirements, it has been desired for an absorbent article to have the following: a back sheet that is soft and yet is not broken even without special reinforcement and also leakproof against liquid and yet highly permeable to moisture, a fastening function that allows unfastening for re-fastening, soft surfaces which are to be brought into contact with the skin (corresponding, in the case of an absorbent article, to the side of the topsheet and the back sheet that is opposite to the side contacting the absorbent member), and a function of minimizing the contact area with the skin. None of the absorbent articles so far proposed satisfy these requirements fully.

Accordingly, an object of the present invention is to provide an absorbent article which has a good fit on a wearer, exhibits excellent leakproofness and breathability while worn, and has an excellent texture.

DISCLOSURE OF THE INVENTION

Extensive investigation was conducted in order to solve the aforesaid problems and found, as a result, that the above object is accomplished by an absorbent article having a male sheet member of a mechanical fastener as a fastening member for fastening the absorbent article. The fastening member is intended to be brought into direct contact with the surface of the back sheet so as to fasten the absorbent article.

The invention has been completed based on the above finding and provides an absorbent article which comprises a liquid permeable topsheet, a liquid impermeable back sheet, and an absorbent member interposed between the topsheet and the back sheet, each of the structures having a substantially rectangular shape, and, while worn, the structures form a front waist body portion located at the front waist of a wearer and a rear waist body portion located at the rear waist of a wearer. The rear waist body portion has at each side thereof a fastening member for fastening the absorbent article, wherein the absorbent article is characterized in that the back sheet is made up of laminated sheeting composed of a finely porous resin film and nonwoven fabric. The fastening member is formed of a male sheet member of a mechanical fastener and designed to be brought into direct contact with the nonwoven fabric constituting the back sheet.

The invention also provides the above-described absorbent article, wherein the finely porous resin film and the nonwoven fabric are laminated one on another with partial adhesion. The adhesion between the finely porous resin film and the nonwoven fabric has a continuous linear pattern which provides a continuous linear adhesive area in high-strength areas. The invention includes high strength areas in a waist area located at the waist of a wearer, leg areas located at each leg of a wearer, and a landing area with which the fastening member is to be brought into contact and a discontinuous dotted pattern and provides a large number of discontinuous dot adhesive areas in areas other than the high-strength areas.

The invention also provides the above-described absorbent article, wherein the linear adhesive area in the linear pattern has the following: a line width of 0.2 to 3 mm, the area ratio of the adhesive area to the non-adhesive area in each high-strength area (the area of the adhesive area:the area of the non-adhesive area) ranges from 5:95 to 70:30, the area of each dot adhesive pattern is 0.05 to 5 mm$^2$, and the area ratio of the adhesive area to the non-adhesive area in each area other than the high-strength areas (the area of the adhesive area:the area of the non-adhesive area) ranges from 1:99 to 40:60.

The invention also provides the above-described absorbent article, wherein the finely porous resin film is made of crystalline polyolefin resin, and the nonwoven fabric is made of polyolefin filaments.

The invention also provides the absorbent article, wherein said nonwoven fabric is made of a mixture of at least two kinds of heat-fusible fibers which are hardly fused together, in which fibers of one kind are strongly fused at their intersections, and the fused intersections are distributed throughout the nonwoven fabric.

The invention also provides the absorbent article, wherein said nonwoven fabric is made of fibers containing at least 50% by weight of heat-fusible conjugated fibers having a core/sheath structure in which the core and the sheath are made of the same type of resinous components and the sheath component has a lower melting point. In addition, the following term "core/sheath type fibers" can be used, instead of the term "fibers having a core/sheath structure".

The invention also provides the above-described absorbent article, wherein the finely porous resin film and the nonwoven fabric are laminated through heat fusing.

The invention also provides the above-described absorbent article, wherein the areas other than the high-strength areas, which high strength areas include a waist body area located at the waist of a wearer, leg areas located at each leg of a wearer, and a landing area. The landing area with which the fastening member is to be brought into contact has a moisture permeability of not less than 0.8 g/[100 cm$^2$·hr].

The term "mechanical fastener" as used herein denotes a fastening member composed of a female sheet member and a male sheet member. The female sheet member comprises a base sheet having thereon filaments arranged to form a large number of loops as female engaging pieces, with at least one end of the individual female engaging pieces being adhered to the base sheet and at least 50% of the female engaging pieces having both ends thereof adhered to the base sheet so as to secure space in the female engaging pieces. The male sheet member comprises a base sheet having thereon a countless number of projections, such as hooks and anchors, as male engaging pieces. The male sheet member and the female sheet member are designed to releasably engage with each other on contact.

In the above-mentioned mechanical fastener, the female sheet member can be replaced with a fibrous sheet, such as general nonwoven fabric.

DETAILED DESCRIPTION OF THE INVENTION

The finely porous resin film and the nonwoven fabric used in the absorbent article of the present invention will be explained at first as follows.

Figure 6A:
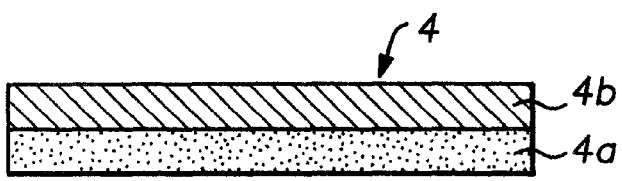
FIGS. 6(a) and 6(b) each schematically show an enlarged cross-sectional view of the back sheet used in the disposable diaper shown in FIG. 4.
Figure 6B:
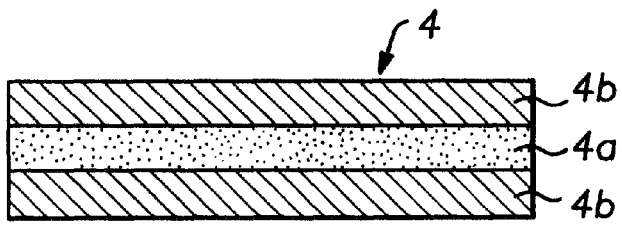

As shown in FIGS. 6(a) and 6(b), the finely porous resin film 4a constituting the back sheet 4 is not particularly restricted in composition and the like as long as it is a leakproof and moisture-permeable resin film, and any known finely porous resin film can be used appropriately.

For example, the resin films described in Japanese Patent Laid-Open Nos. 47031/90, 75151/90, and 331306/93 as cited above can be used. When the resin film described in these publications is used, the resin film is preferably used with a small thickness as described below. Insufficiency of tensile and tear strength of such a thin film could be compensated for by the nonwoven fabric laminated thereon.

The finely porous resin film preferably has a thickness of 5 to 100 μm, particularly 10 to 40 μm, a moisture permeability of not less than 0.8 g/[100 cm²·hr], particularly 1.0 to 3.0 g/[100 cm²·hr], and a leakproofness of not less than 30 minutes, still preferably not less than 60 minutes, particularly preferably not less than 120 minutes, as tested with artificial urine having a surface tension of 45 dyne/cm at a liquid pressure of 35 g/cm² (refer to the test of leakproofness in Example hereinafter described).

In the present invention the following finely porous resin films are used for preference.

Finely porous resin films are made of crystalline polyolefin resins, such as a crystalline high-density polyethylene resin and a crystalline polypropylene resin, particularly crystalline propylene homopolymer resins, especially crystalline propylene homopolymer resins having a melt index of 5 or less.

The above-mentioned finely porous resin films do not contain those additives that have conventionally been used for making pores, such as fillers and plasticizers, but contain, if desired, only a small amount of stabilizers (e.g., antioxidants) for stabilization of the aforesaid specific crystalline polyolefin resins and a small amount of colorants or shielding agents for coloring or hiding.

The finely porous resin film can be obtained by molding the above-described crystalline polyolefin resin into a film by a conventional method known for preparing a thermoplastic resin film, such as blown film extrusion and T-die extrusion, and subjecting the resulting film successively to heat treatment (hereinafter referred to as a heat treatment step (1)), stretching (hereinafter referred to as a stretching step), and heat treatment (hereinafter referred to as a heat treatment step (2)).

The molding into a film, for example, by blown film extrusion is preferably carried out at a draft ratio of 20 or higher, more preferably 40 or higher; a blow-up ratio of 0.7 to 1.2, more preferably 0.8 to 1.1; a take-up speed of 5 to 100 m/min, more preferably 10 to 50 m/min; and at a molding temperature higher than the melting point by 30 to 100° C., more preferably at a temperature higher than the melting point by 50 to 80° C. The draft ratio and the blow-up ratio denote the values represented by the following respective formulae:

Draft ratio=take-up speed/linear velocity of a resin as extruded from a die

Blow-up ratio=diameter of blown film/diameter of die lip (through which a resin is extruded)

The heat treatment step (1) facilitates fine pore formation in the subsequent stretching step.

The heat treatment step (1) can be carried out by any of known methods, for example, a method of contacting a sheet with a heated roll or metal plate, a method of heating a sheet in air or an inert gas, or a method of heating a sheet wound around a core in a gas phase, and the like.

The temperature and heat conditions in the heat treatment step (1) depend on the kind of crystalline polyolefin used. The temperature is preferably lower than the melting point by 10 to 80° C., and the time is preferably 10 seconds to 10 hours.

In the stretching step the heat-treated film obtained in the heat treatment step (1) is stretched to obtain a film having fine pores (hereinafter referred to as a porous film).

The method of stretching in the stretching step is not particularly limited. The stretching can be carried out by a known method, such as roll stretching or tentering.

The stretching conditions in the stretching step (i.e., stretching temperature and stretch ratio) vary depending on the kind of the crystalline polyolefin resin, the desired moisture permeability, and the like. The stretching temperature is preferably lower than the melting point by 50 to 130° C., and the stretch ratio is preferably 50 to 500% (the language "stretch ratio of 50%" as used herein means that a length 100 before stretching becomes 150 after stretching).

In the heat treatment step (2) the porous film is further subject to a heat treatment.

The temperature in the heat treatment step (2) varies depending on the kind of the crystalline polyolefin resin and preferably ranges from a temperature higher than the stretching temperature by 10° C. or more to a temperature lower than the melting point by 10° C.

The heat treatment step (2) is preferably carried out while controlling the tension so that the porous film may be reduced in length preferably by 5 to 50%, still preferably 10 to 40%, based on the length before the heat treatment step (2).

Any kind of nonwoven fabric can be used as the nonwoven fabric constituting the back sheet 4 with no particularly limitation as long as it is usable in common absorbent articles, such as disposable diapers. Useful nonwoven fabric includes one prepared by cutting filaments formed of a single thermoplastic resin, e.g., polyethylene, polypropylene, polyethylene terephthalate or polyamide, or conjugated filaments having a core/sheath structure or a side-by-side structure, if desired, after drawing and crimping the filaments by general melt-spinning, and bonding the resulting short fibers by dot adhesion with heat or an adhesive, one prepared by interlocking the short fibers by means of a water jet stream, a needle, etc., i.e., nonwoven fabric formed by a wet process, a dry process, spun-lacing or spun-bonding, etc. Nonwoven fabric comprising divided filaments obtained by dividing multilayer filaments by an outer force can also be used. Further, nonwoven fabric directly formed by a melt-blown process can be used.

Of these kinds of nonwoven fabric, the one prepared by using core/sheath type conjugated filaments having a low-elastic and/or low melting point resin as a sheath is preferred not only for its satisfactory texture and elasticity but also because laminating on the finely porous resin film can be conducted simply by heat fusing, which brings advantages in productivity, safety and economy. The core/sheath type conjugated filaments used include polyolefin filaments, such as polyethylene terephthalate (PET)/polyethylene (PE), polypropylene (PP)/polyethylene (PE), and polypropylene (PP)/polypropylene (PP).

The filaments for use in the nonwoven fabric preferably have as small a thickness as possible for the softness and texture of the resulting nonwoven fabric. A particularly preferred thickness is 3 denier or less. While not particularly limiting, the lower limit of the thickness is about 0.1 denier. Filaments finer than this lower limit are difficult to produce. The nonwoven fabric preferably has a basis weight of 5 to 200 g/m², particularly 10 to 50 g/m², and an apparent thickness of 15 to 700 μm, particularly 30 to 400 μm, the apparent thickness being defined to be the thickness of a sample sandwiched in between a platen and a 10 cm×10 cm plate with a load of 0.5 gf/cm² put on the plate, as measured with PA-1830, a measuring device manufactured by Keyence.

The nonwoven fabric can also be one made of a mixture of at least two kinds of heat-fusible fibers which are hardly fused together.

The language "hardly fused together" as used herein means that the fibers of two kinds are not fused together or, they are fused with only a smaller bonding strength than would be obtained among fibers of the same kind, when they are exposed to such a condition that causes fibers of the same kind be fused together.

The two kinds of heat-fusible fibers which are hardly fused together are not particular limited as long as they are hardly fused together. They are preferably selected from the group consisting of a core/sheath type fiber having low melting point polypropylene as a sheath, a core/sheath type fiber having polyethylene as a sheath, and a core/sheath type fiber having low melting point polyester as a sheath.

When a core/sheath type fiber having low melting point polypropylene as a sheath, for instance, is used as one of the two kinds of fibers (hereinafter referred to as fiber A), the other kind of fibers (hereinafter referred to as fiber B) is preferably a core/sheath type fiber having polyethylene as a sheath or a core/sheath type fiber having low melting point polyester as a sheath.

It is preferable to use a core/sheath type fiber having low melting point polypropylene as a sheath as a fiber A for obtaining nonwoven fabric having sealing properties and strength, and to use a core/sheath type fiber having polyethylene as a sheath as a fiber B for obtaining nonwoven fabric having a good texture and strength.

The low melting point polypropylene, which is used as a sheath component of the core/sheath type fiber having low melting point polypropylene as a sheath, is not particularly limited and can be any conventional low melting point polypropylene. The melting point of the low melting point polypropylene is preferably 130 to 150° C. The core component of the above fiber can be polyethylene terephthalate (melting point: 250 to 270° C.) or polypropylene (melting point: 150 to 170° C.), etc.

The fiber preferably comprises 30 to 70 parts by weight of the sheath and 30 to 70 parts by weight of the core. For obtaining high fusion strength, the fiber still preferably comprises 50 to 70 parts by weight of the sheath and 30 to 50 parts by weight of the core.

Commercially available core/sheath type fibers having low melting point polypropylene as a sheath, such as a series of SP fibers (e.g., NBF(SP), produced by Daiwabo Co., Ltd.), a series of TPC fibers (e.g., TPC, produced by Chisso Corp.), and a series of PR-P (e.g., PR, produced by Ube Nitto Kasei K.K.), can be used.

The polyethylene which can be used in the core/sheath type fiber having polyethylene as a sheath is preferably one having a melting point of 120 to 140° C. The core component in this type of fiber includes polyethylene terephthlate (melting point: 250 to 270° C.) and polypropylene (melting point: 150 to 170° C.), etc.

The fiber preferably comprises 30 to 70 parts by weight of the sheath and 30 to 70 parts by weight of the core. For obtaining high fusion strength, the fiber still preferably comprises 50 to 70 parts by weight of the sheath and 30 to 50 parts by weight of the core.

Commercially available core/sheath type fibers having polyethylene as a sheath, such as a series of F6 fibers (e.g., TJ04CE, produced by Teijin Ltd.), a series of ETC fibers (e.g., ETC, produced by Chisso Polypro K.K.), and a series of SH fibers (e.g., NBF(SH), produced by Daiwabo Co., Ltd.), can be used.

The low melting point polyester which is used as a sheath component of the core/sheath type fiber having low melting point polyester as a sheath is not particularly limited and can be any conventional low melting point polyester. The melting point of the low melting point polyester is preferably 100 to 150° C. The core component of the above fiber includes polyethylene terephthlate (melting point: 250 to 270° C.) and polypropylene (melting point: 150 to 170° C.), etc.

The fiber preferably comprises 40 to 90 parts by weight of the sheath and 10 to 60 parts by weight of the core. The fiber still preferably comprises 50 to 90 parts by weight of the sheath and 10 to 50 parts by weight of the core.

Commercially available core/sheath type fibers having low melting point polyester as a sheath, such as a series of ELK fibers (e.g., ELK, produced by Teijin Ltd.), a series of TBF fibers (e.g., TBF, produced by Teijin Ltd.), and a series of Melty fibers (e.g., MELTY 4080, produced by Unitika, Ltd.), can be employed.

The fibers used as fiber A and those used as fiber B may be the same or different in fiber thickness (fineness). A preferred fiber thickness is 2 to 15 denier, particularly 3 to 6 denier.

If the fiber thickness is less than 2 denier, where the resulting nonwoven fabric is used as a female member of a mechanical fastener, the space among the fibers into which engaging pieces of a male member can enter and be caught will be reduced. Further, the bonding strength (fusion strength) per intersection of fibers of the same kind is reduced, leading to a reduction in force of fastening a male member when the nonwoven fabric is used as a female member. If the fiber thickness exceeds 15 denier, although the bonding strength per intersection of fibers increases, such fibers are stiff and only provide weak engagement with the male member.

The fibers A and B may have the same or different fiber lengths. A preferred fiber length is 40 to 80 mm.

While the mixing ratio of fibers A and B is arbitrary depending on the fibers, the fiber A is preferably used in a proportion of 30 to 70 parts by weight per 100 parts by weight of the total weight of the fibers A and B. This preferred range also applies when nonwoven fabric A further comprises fiber C as hereinafter described.

More specifically, where the fiber A is a core/sheath type fiber having low melting point polypropylene as a sheath and the fiber B is a core/sheath type fiber having polyethylene as a sheath, the fiber A is preferably used in a proportion of 30 to 70 parts by weight per 100 parts by weight of the total weight of the fibers A and B.

If the proportion of the fiber A is less than 30 parts by weight or more than 70 parts by weight, the fiber has a reduced degree of freedom and provides substantially nothing more than nonwoven fabric made up of a single kind of fiber.

The nonwoven fabric can further contain an additional fiber which is hardly fused with either of the two kinds of fibers, i.e., fibers A and B (hereinafter referred to as fiber C).

The fiber C is preferably selected from the group consisting of core/sheath type fiber having low melting point polypropylene as a sheath, core/sheath type fiber having polyethylene as a sheath, and core/sheath type fiber having low melting point polyester as a sheath.

For example, when using core/sheath type fibers having a low melting point polypropylene as a sheath as fiber A and core/sheath type fiber having polyethylene as a sheath as fiber B, it is preferable to use core/sheath type fiber having low melting point polyester as a sheath as fiber C.

A three-component system nonwoven fabric made up of a mixture of the above-mentioned three kinds of fibers has an increased degree of freedom of constituent fibers as compared with two-component system nonwoven fabric while retaining an adequate fiber density.

The thickness and length of the fiber C can be selected appropriately from the ranges given as for the fibers A and B.

The proportion of the fiber C, if used, is preferably 20 to 40 parts by weight per 100 parts by weight of the total weight of the fibers A, B, and C. More specifically, in using a core/sheath type fiber having low melting point polypropylene as a sheath as fiber A, core/sheath type fiber having polyethylene as a sheath such as fiber B, and core/sheath type fiber having low melting point polyester as a sheath such as fiber C, a preferred proportion of the fiber C is 20 to 40 parts by weight per 100 parts by weight of the total weight.

If desired, the nonwoven fabric may further contain other kinds of fibers that are hardly fused with any of the above-described three kinds of fibers.

The nonwoven fabric comprising a mixture of various fibers preferably has a basis weight of 20 to 50 g/m$^2$ and a fiber density of 0.01 to 0.05 g/cm$^3$.

In the nonwoven fabric, fibers of one kind are strongly fused at their intersections, and the fused intersections are uniformly distributed throughout the nonwoven fabric.

Figure 1:
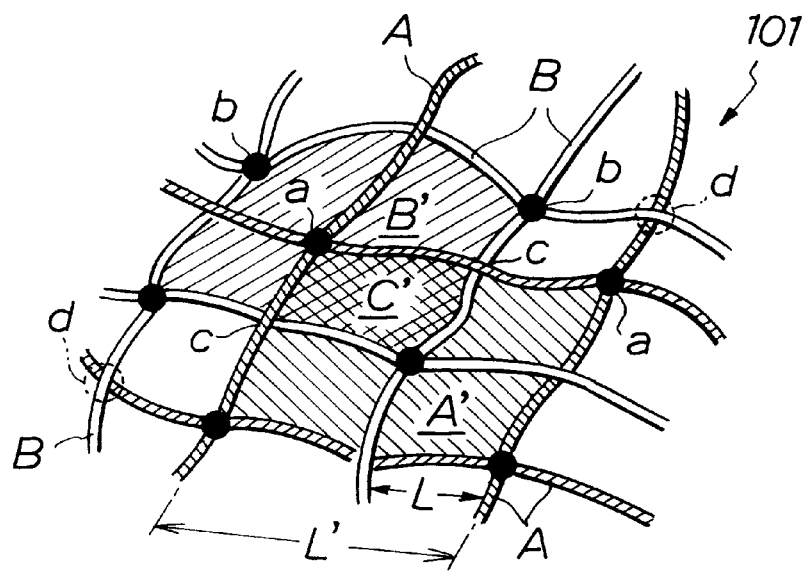
FIG. 1 is a schematic illustration showing the structure of the individual fibers in the nonwoven fabric which is preferably used in the invention.
Figure 2:
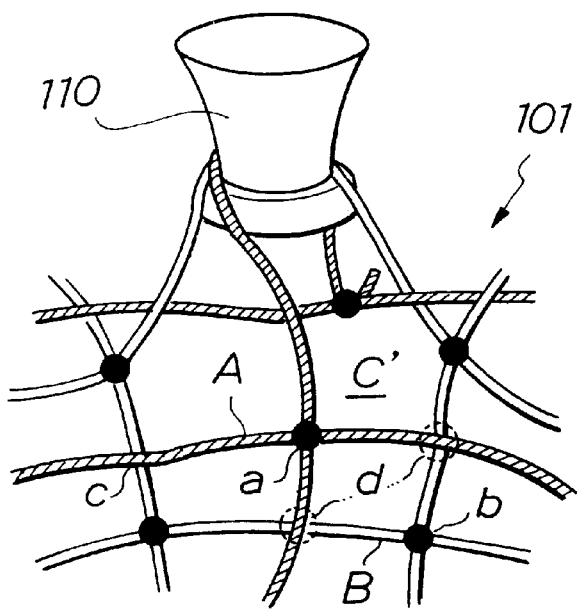
FIG. 2 is a schematic illustration showing the state in which an engaging piece of a male member of a mechanical fastener bites the nonwoven fabric shown in FIG. 1.

The above-mentioned structure formed of different fibers in the nonwoven fabric is explained in more detail by referring to FIGS. 1 and 2.

FIG. 1 schematically illustrates the structure of the individual fibers in an embodiment of the nonwoven fabric, and FIG. 2 schematically illustrates the state in which an engaging piece of a male member of a mechanical fastener bites the nonwoven fabric.

While the following description relates to a two-component system nonwoven fabric comprised of fibers A and B, it applies to systems comprised of three or more components.

Nonwoven fabric 101 shown in FIG. 1 is comprised of fibers A and B which are hardly fused together.

In the nonwoven fabric 101, the fibers A are strongly fused among themselves at their intersections a, and the fibers B are strongly fused among themselves at their intersections b.

The intersections a and b are distributed throughout the nonwoven fabric 101 almost uniformly.

The term "almost uniformly" as used above is intended to mean that the intersections are equally present throughout the nonwoven fabric 101. The number of the total intersections (a+b) per unit area is preferably $2.5 \times 10^6$ to $1.0 \times 10^8$ per m$^2$.

The words "strongly fused" as used herein means that the fusion between fibers of the same kind has a single fiber fusion bonding strength of 3 gf or more. The "single fiber fusion bonding strength" can be measured as follows.

Method of Measurement of Single Fiber Fusion Bonding Strength

Figure 3A:
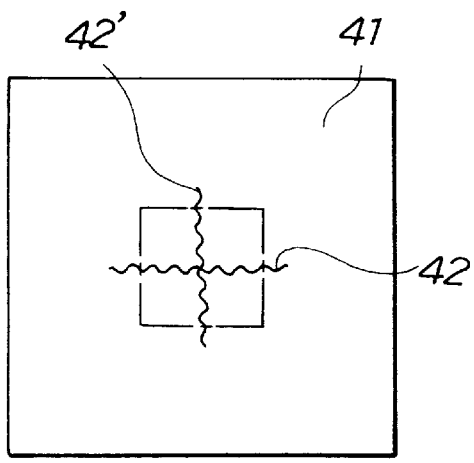
FIGS. 3(a) to 3(c) show a method for measuring a single fiber fusion bonding strength (or a fused point strength).

FIG. 3(a) is referred to. A paper frame 41 having a square cut out of its central portion (indicated by a single-dotted chain dash in FIG. 3(a)) is prepared. Two single fibers 42 and 42' are set at right angles in such a manner that the intersection is positioned at the center of the square, and both ends of the two fibers are adhered to the paper frame 41 with an adhesive. Hot air at a working temperature of 143° C. is blown against the fibers 42 and 42' adhered to the paper frame 41 at a flow of 2.3 m/sec for 12 seconds to fuse the fibers at the intersection.

Figure 3B:
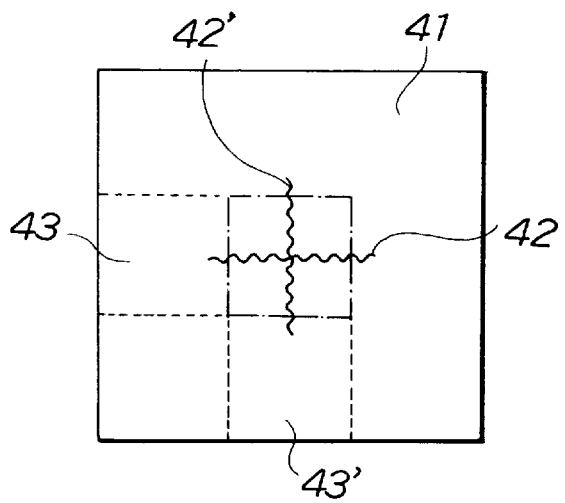
Figure 3C:
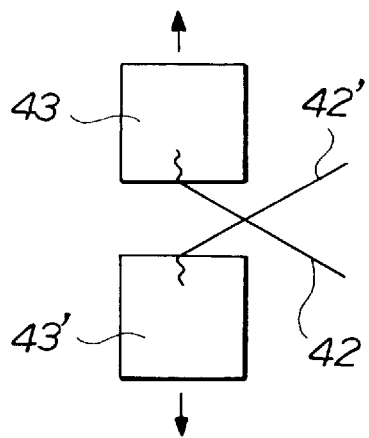

The paper frame 41 is cut along the dotted line as shown in FIG. 3(b) to cut out square pieces 43 and 43' on which one end of the fibers 42 and 42' is adhered, respectively, as shown in FIG. 3(c). The pieces 43 and 43' are pulled to the respective directions shown in FIG. 3(c) at a speed of 50 mm/min, and the strength of the intersection is measured as a single fiber fusion bonding strength.

As shown in FIG. 1, the nonwoven fabric 101 has meshes A' and B' formed of the respective fibers of one kind, each mesh A' being surrounded by the fibers A and intersections a and each mesh B' being surrounded by the fibers B and intersections b.

The nonwoven fabric 101 also has a number of non-fusion bonded intersections c at which the fibers A and B are intersecting without being bonded together and a number of weakly fusion bonded intersections d at which the fibers A and B are weakly fusion bonded together.

The words "weakly bonded" as referred to above is used for the fusion bonding between different kinds of heat-fusible fibers and means that the single fiber fusion bonding strength is 2 gf or lower.

Deformable and expandable meshes C' are also formed by the intersections a and b and the non-fusion bonded intersection c and/or the weakly fusion bonded intersection d. That is, each mesh C' corresponds to an overlap of one mesh A' of one kind and one mesh B' of another kind, i.e., an overlap of two meshes of different kinds of fibers, and comprises the intersections a, the intersection b, and the non-fusion bonded intersection c or (in an embodiment not shown) the weakly fusion bonded intersection d.

The individual fibers A and B in the nonwoven fabric 101 have a high degree of freedom because of the non-fusion bonded intersections c and also because the weakly fusion bonded intersections d are easily undone by a weak stress and act similarly to the non-fusion bonded intersections c. For example, when the nonwoven fabric 101 is used as a female member of a mechanical fastener, the weakly fused-bonded intersections d function like the non fused-bonded intersections c. Accordingly, the meshes A' and B' each formed of the respective kind are deformable, and the meshes C' are not only deformable but expandable.

That is, even though the fiber density of the nonwoven fabric 101 is made equal to or higher than that of general nonwoven fabric so that the distance L' between individual fibers is equal to or less than that of general nonwoven fabric, the meshes C' are free in deforming and expanding owing to the high freedom of the fibers A and B.

In other words, the above-described mesh structure allows the nonwoven fabric 101 to have an equal or even higher fiber density than that of general nonwoven fabric and still to have a larger fiber distance between fibers of the same kind (i.e., the distance between fusion-bonded fibers of the same kind, indicated by symbol L' in FIG. 1) than that in general nonwoven fabric. The fiber distance between fibers of the same kind in the nonwoven fabric 101 having a fiber A to fiber B ratio of 1:1, for instance, is about twice that in general nonwoven fabric made of a single kind of fiber and having the same fiber density.

Owing to the sufficient distance between fibers, the freedom of meshes A' and B' in deforming, and the freedom of meshes C' in deforming and expanding, a male engaging piece 110 of a male sheet member can smoothly enter the space between fibers A and A, between fibers B and B or between fibers A and B, i.e., into the mesh A' or B' formed of the same kind of fibers or the mesh C', thereby being anchored by the fibers A and B.

Particularly because of the high degree of freedom of the mesh C' in deforming and expanding, it is easy for the engaging piece 110 to enter the space of the mesh C' and thereby to be anchored by the fibers with ease.

Since the individual constituent fibers have a higher degree of freedom than in nonwoven fabric made of a single kind of fiber, it is possible for one male engaging piece 110 be anchored by two or more fibers as shown in FIG. 2. In this case, the mechanical fastener has an improved peel strength compared to a nonwoven fabric made of a single kind of fiber, and fluffing of the nonwoven fabric can be suppressed on peeling the male member.

The peel strength between the male member and the nonwoven fabric can further be increased by using fibers having a high fusion bonding strength (for example, fibers having an increased proportion of the sheath component) as fibers A or B.

The fiber distance L between fibers A and B is preferably 50 to 800 µm, while varying depending on the kind, number, mixing ratio, and fiber density of the fibers used.

It is preferable that the nonwoven fabric 101 has a tensile strength of 1000 gf/50 mm or more in the MD direction (machine direction) and 200 gf/50 mm or more in the CD direction (cross direction of MD).

The terminology "tensile strength" as used herein is a value obtained by the following method of measurement.

Method of Measurement of Tensile Strength

A tensile tester TENSILON RTA-100, manufactured by Orientec K.K. is used. A 50 mm wide and 200 mm long specimen is cut out of nonwoven fabric, set between chucks at a distance of 75 mm, and pulled at a pulling speed of 300 mm/min. The stress at break was measured.

Measurement was taken 10 times for every sample in each of MD and CD directions, and an average was obtained for each direction.

The nonwoven fabric can be prepared as follows.

The nonwoven fabric comprised of two kinds of fibers, i.e., fibers A and B, can easily be obtained by an air-through method, in which hot air at 130 to 150° C. is blown against a fiber web, which is prepared from a mixture of the fibers in a usual manner, at an air flow of 1 to 2 m/sec for 5 to 10 seconds.

The nonwoven fabric comprised of three or more kinds of fibers can easily be obtained by forming a mixture of the fibers into a fiber web and treating the fiber web by an air-through method in the same manner as stated above.

The nonwoven fabric can also be obtained easily by a method for preparing general nonwoven fabric, such as embossing.

In the present invention, nonwoven fabric containing a specific amount of a specific heat-fusible conjugated fiber is hereinafter referred to as nonwoven fabric BB.

The specific heat-fusible conjugate fiber which can be used in the nonwoven fabric BB is a core/sheath type fiber in which the core and the sheath are made of the same type of resinous components and the sheath component has a lower melting point.

The language "the same type of resinous components" as used above is intended to mean that the resinous component constituting the sheath and that constituting the core have a similar structure, i.e., the same main structure, and are compatible with each other. For example, a polypropylene (PP) core and a low melting point PP sheath are combined, or a polyethylene terephthalate (PET) core and a low melting point PET sheath are combined. The combination of the core and the sheath is not limited to these examples, and any combination can be used provided that the core component and the sheath component are combined so as to satisfy the condition that the interfacial strength between the core and the sheath is not lower than the fused point strength and that the fused point strength is higher than 3 gf.

"The same type of resinous components" can be resin mixtures (so-called polyblends). For example, the core component can be PET while the sheath component can be a resin mixture mainly comprising PET, or the core component can be PP while the sheath component can be a resin mixture mainly comprising PP. The resin mixture mainly comprising PET includes a resin mixture comprising 100 parts by weight of PET and not more than 100 parts by weight of polyethylene (PE). The resin mixture mainly comprising PP includes a resin mixture comprising 100 parts by weight of PP and 2 to 8 parts by weight of PE. And, the core component can be a resin mixture of the above-mentioned resins, e.g., PP and PET.

A core to sheath weight ratio of the heat-fusible conjugate fiber is preferably 20:80 to 80:20, still preferably 20:40 to 80:60.

The melting point of the core component is preferably higher than that of the sheath component by 10 to 120° C. More specifically, it is preferable that the melting point of the core component is 125 to 260° C. and that of the sheath component is 90 to 150° C.

Examples of the above-described heat-fusible conjugate fiber include a PP/PP core/sheath fiber composed of a polypropylene core having a melting point of 150 to 170° C. and a low melting point polypropylene sheath whose melting point is from 130 to 150° C. and lower than that of the core; a PE/PE core/sheath fiber composed of a polyethylene core having a melting point of 120 to 140° C. and a polyethylene sheath having a melting point of 90 to 120° C.; and a PET/PET core/sheath fiber composed of a polyethylene terephthalate core having a melting point of 250 to 270° C. and a polyethylene terephthalate sheath having a melting point of 70 to 180° C., etc.

The low melting point polypropylene which can be used as a sheath component in the PP/PP core/sheath fiber can be any known low melting point polypropylene. The fiber preferably comprises 30 to 70 parts by weight of the sheath and 30 to 70 parts by weight of the core in the above PP/PP core/sheath type fiber. For obtaining high fusion bonding strength, the fiber still preferably comprises 40 to 60 parts by weight of the sheath and 40 to 60 parts by weight of the core.

Commercially available PP/PP core/sheath fibers, such as a series of TPC fibers (e.g., TPC, produced by Chisso Corp.), and a series of PR-P fibers (e.g., PR, produced by Ube Nitto Kasei K.K.), can be used.

Polyethylene for use as a sheath component in the PE/PE core/sheath fiber can be any known polyethylene. The fiber preferably comprises 30 to 70 parts by weight of the sheath and 30 to 70 parts by weight of the core in the above PE/PE core/sheath fiber. For obtaining high fusion bonding strength, the fiber still preferably comprises 40 to 60 parts by weight of the sheath and 40 to 60 parts by weight of the core.

The low melting point polyester for use as a sheath component in the PET/PET core/sheath fiber can be any low melting point polyester. The PET/PET core/sheath fiber preferably comprises 40 to 90 parts by weight of the sheath and 10 to 60 parts by weight of the core in the above PET/PET core/sheath type fiber. The fiber still preferably comprises 50 to 90 parts by weight of the sheath and 10 to 50 parts by weight of the core.

Commercially available core/sheath fibers having low melting point polyester as a sheath, such as a series of ELK fiber (e.g., ELK, produced by Teijin Ltd.), a series of TBF fibers (e.g., TBF, produced by Teijin Ltd.), and a series of Melty fibers (e.g., MELTY 4080, produced by Unitika Ltd.), can be employed.

The heat-fusible conjugated fiber preferably has a fiber thickness of 2 to 12 denier, more preferably 4 to 10 denier, and a fiber length of 3 to 10 cm, more preferably 4 to 8 cm.

The heat-fusible conjugate fiber preferably has a fused point strength of 3 gf or higher, particularly 5 gf or higher. The higher the fused point strength, the better. The interfacial strength between the core and the sheath is preferably higher than the fused point strength (the strength at the intersection of the individual heat-fusible conjugate fibers).

If the fused point strength is less than 3 gf, when the nonwoven fabric is used as a female member of a mechanical fastener, the fused points of the individual constituent fibers tend to be broken on stripping a male member, which causes fluffing.

The term "fused point strength" as used herein means a value measured in the same manner as for the single fiber fusion bonding strength.

The nonwoven fabric BB contains at least 50% by weight, preferably 70 to 100% by weight, of the heat-fusible conjugate fiber. If the content of the heat-fusible conjugate fiber is less than 50% by weight, the fused point strength is insufficient, and the nonwoven fabric BB undergoes fluffing when used as a female member of a mechanical fastener.

That is, the nonwoven fabric BB may consist solely of the heat-fusible conjugate fiber or a fiber mixture comprising at least 50% by weight of the heat-fusible conjugate fiber and other fibers.

The other fibers which may be used in combination with the heat-fusible conjugate fiber include a general polyester fiber, a general polypropylene fiber, a general rayon fiber, a general acrylic fiber, general cotton fiber, a general nylon fiber, a general PP/PE core/sheath type conjugate fiber, a general PET/PE core/sheath type conjugate fiber, and a general polyvinyl alcohol (PVA) fiber, etc.

The nonwoven fabric BB comprised of the above-described fibers is explained in greater detail.

The nonwoven fabric BB is one made up of the above-described constituent fibers. In the nonwoven fabric BB, the individual heat-fusible conjugate fibers are preferably fused at their intersections.

The language "fused at their intersections" as used above does not mean that the fibers are fused only at their intersections nor the fibers are fused at all their intersections but does mean that the fibers are fused at least at part of their intersections.

The nonwoven fabric BB is obtained by subjecting a web composed of the above fibers to a heat treatment. The areal shrinkage percentage of the web due to the heat treatment is preferably less than 10%. The smaller the shrinkage, the better (the areal shrinkage percentage is idealy 0%).

If the areal shrinkage percentage exceeds 10%, the fibers lose nerve and the nonwoven fabric is hardened due to shrinkage. When such nonwoven fabric is used as a female member of a mechanical fastener, sufficient space for receiving a male member cannot be assured, and the peeling strength is small.

The areal shrinkage percentage can be controlled by, for example, decreasing the draw ratio in fiber production, using a highly stiff resinous material as a core component, using a low melting point resinous material as a sheath component, using, as resinous components of constituent fibers, resins which hardly undergo intermolecular strain when heat treated, or the like means. The areal shrinkage percentage can also be controlled by adjusting the processing conditions of nonwoven fabric, for example, by setting the heat treatment low and increasing the hot air flow.

The areal shrinkage percentage can be measured as follows.

Method of Measurement of Areal Shrinkage Percentage

Fiber is made into a 30 cm wide and 45 cm long web having a basis weight of 30 g/m$^2$. Two marks are put on the central part of the web at an interval of 20 cm in each of the longitudinal direction and the width direction. The web is then subjected to a heat treatment with hot air at 120° C. for 1 minute, and the distance between the two marks in each direction was measured after the heat treatment. The measured values are applied to equation (1) shown below to obtain the areal shrinkage percentage.

$$\text{Areal shrinkage percentage}(\%) = [1 - (L_{A2} \times L_{B2})/(L_{A1} \times L_{B1})] \times 100 \quad (1)$$

wherein $L_{A1}$ is a distance between the two marks in the longitudinal direction before heat treatment; $L_{A2}$ is a distance between the two marks in the longitudinal direction after heat treatment; $L_{B1}$ is a distance between the two marks in the width direction before heat treatment; and $L_{B2}$ is a distance between the two marks in the width direction after heat treatment.

The nonwoven fabric BB preferably has a tensile strength of 1000 gf/50 mm or more in the MD direction (machine direction) and 200 gf/50 mm or more in the CD direction (cross direction of MD).

The terminology "tensile strength" as used herein is a value obtained by the following method of measurement.

Method of Measurement of Tensile Strength

A tensile tester TENSILON RTA-100, manufactured by Orientec K.K. is used. A 50 mm wide and 200 mm long specimen is cut out of nonwoven fabric, set between chucks at a distance of 75 mm, and pulled at a pulling speed of 300 mm/min. The stress at break was measured.

Measurement was taken 10 times for every sample in each of MD and CD directions, and an average was obtained for each direction.

The nonwoven fabric BB preferably has a basis weight of 20 to 50 g/m$^2$ and a fiber density of 0.01 to 0.05 g/cm$^3$.

The nonwoven fabric BB can easily be obtained by making the constituent fibers into a web and subjecting the resulting web to a heat treatment in a usual manner.

It is particularly preferable in the invention that the finely porous resin film is made of the crystalline polyolefin resin, and the nonwoven fabric is fabricated from the polyolefin filament, or is either the nonwoven fabric 101 or BB.

The absorbent article according to the present invention is described in detail by referring to the accompanying drawings.

Figure 4:
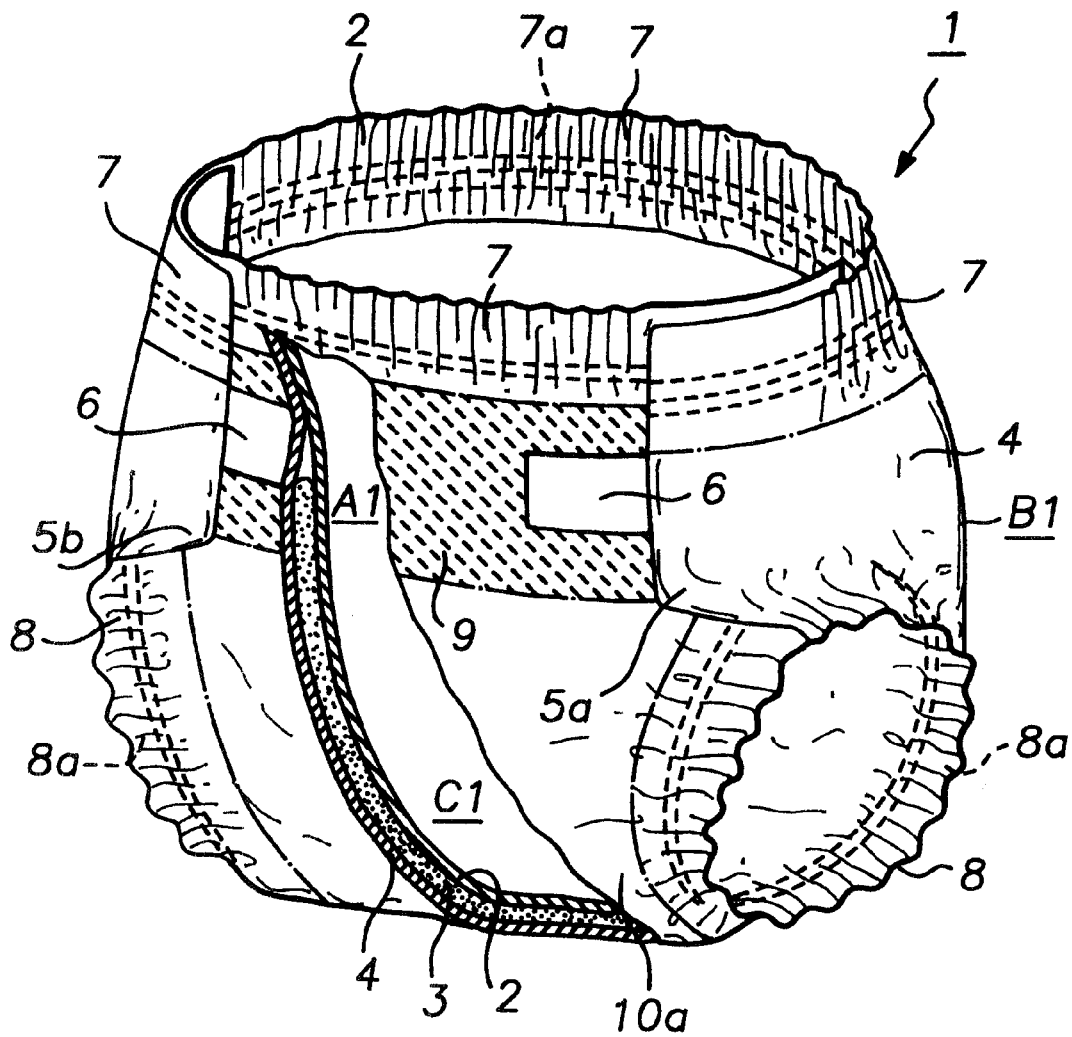
FIG. 4 is a perspective view with several cutaway portions of a disposable diaper as an embodiment of the absorbent article according to the invention.
Figure 5:
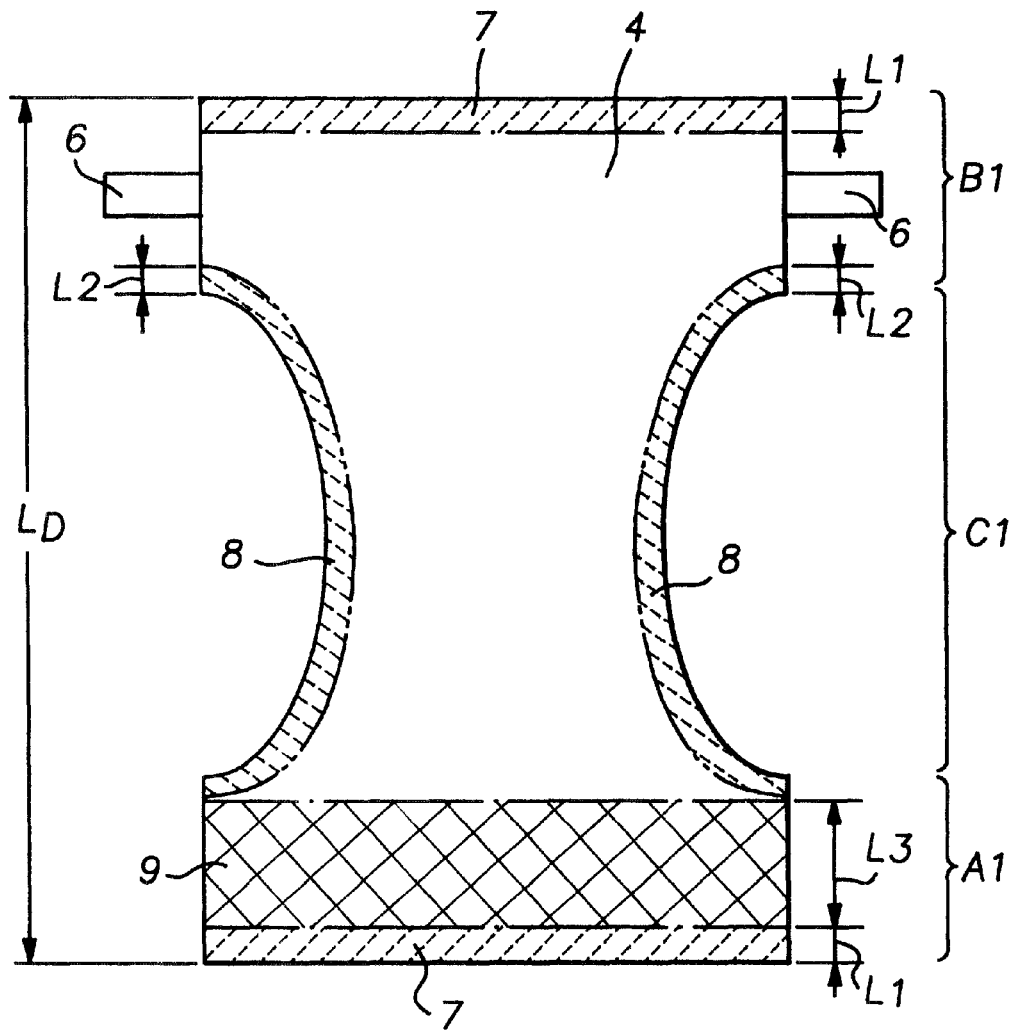
FIG. 5 is a plane view of the disposable diaper shown in FIG. 4 in its unfolded condition as seen from the back sheet side thereof.
Figure 7:
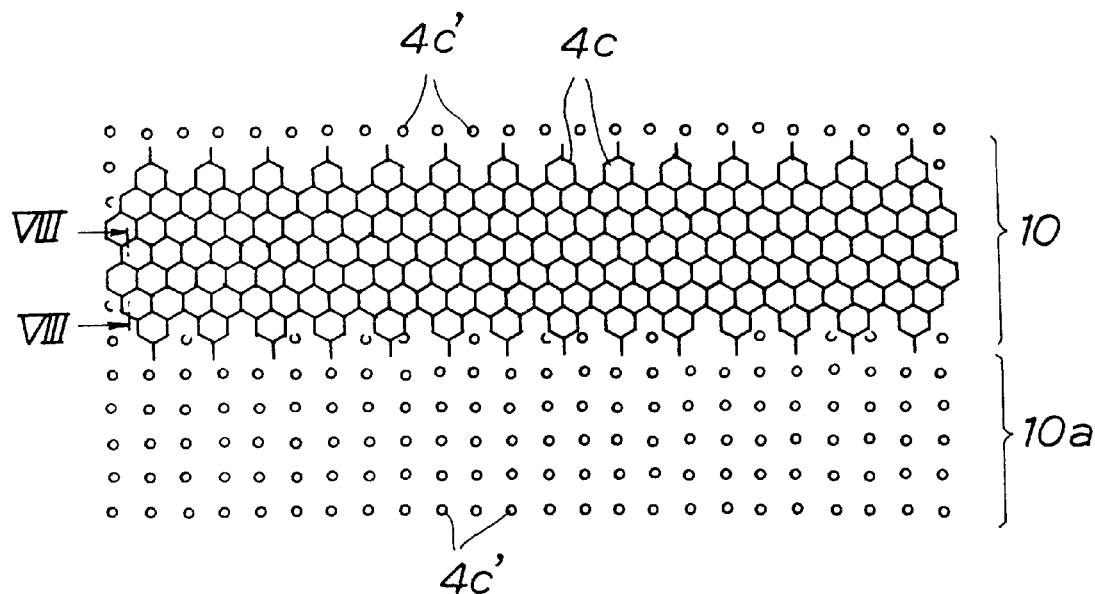
FIG. 7 is a plane view illustrating the adhesion pattern of the back sheet shown in FIGS. 6(a) and 6(b).
Figure 8:
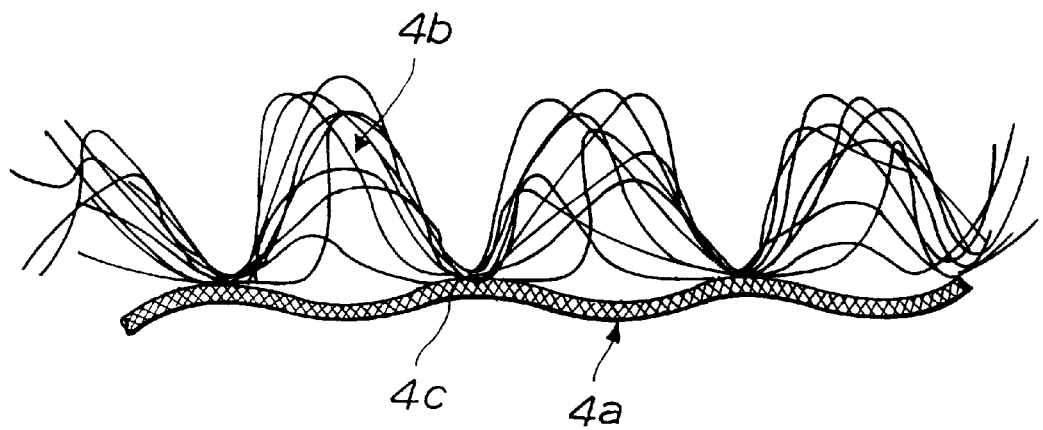
FIG. 8 is an enlarged cross-sectional view of FIG. 7 along line VIII—VIII.

FIG. 4 is a perspective view with several cutaway portions of a disposable diaper as an embodiment of the absorbent article of the invention. FIG. 5 is a plane view of the disposable diaper shown in FIG. 4 in its unfolded conditions as seen from the back sheet side thereof. FIGS. 6(*a*) and 6(*b*) each schematically show an enlarged cross-sectional view of the back sheet used in the disposable diaper shown in FIG. 4. FIG. 7 is a plane view illustrating the adhesion pattern of the back sheet shown in FIG. 6(*a*) and 6(*b*). FIG. 8 is an enlarged cross-sectional view of FIG. 7 along line VIII—VIII. FIGS. 9(*a*) and 9(*b*) each schematically show an enlarged cross-sectional view of the male sheet member of a mechanical fastener.

The disposal diaper 1 shown in FIGS. 4 and 5, illustrations of an absorbent article, comprises a liquid permeable topsheet 2, liquid impermeable back sheet 4, and an absorbent member 3 which is interposed between the topsheet 2 and the back sheet 4. The disposable diaper 1 forms a substantially rectangular shape and, while worn, is sectioned into a front waist body portion A1 located at the front waist of a wearer and a rear waist body portion B1 located at the rear waist of a wearer. The rear waist body portion B1 has a fastening member 6 for fastening the absorbent article at both side edges thereof 5a and 5b.

In more detail, the front waist body portion A1 has a landing area 9 with which the fastening member 6 is to be brought into contact when the diaper is fastened. A crotch portion C1 is formed between the front waist body portion A1 and the rear waist body portion C1 which corresponds to the crotch portion of a wearer.

The back sheet 4 and the topsheet 2 are longer and wider than the absorbent member 3. The back sheet 4 and the topsheet 2 are adhered to each other at the periphery of the absorbent member 3 interposed between these two sheets. The absorbent member 3, the back sheet 4, and the topsheet 2 each have the middle portion thereof narrowed to form the crotch portion C1 that is narrower than the front waist body portion A1 and the rear waist body portion B1.

Elastic members 7a and 8a are provided in the waist area 7 and the leg area 8 which are located at the waist and each leg of a wearer thereby giving a further improvement in leakproof function when worn. Such a structure is the same as in conventionally known absorbent articles, such as disposable diapers.

Topsheets and absorbent members used in common absorbent articles, such as disposable diapers, can be used as the topsheet 2 and the absorbent member 3 with no particular limitation. Elastic members, such as bands or stretchable rubber, which are used in common absorbent articles, such as disposable diapers, can be used as the elastic members 7a and 8a with no particular limitation.

In the disposable diaper 1 according to this embodiment, the back sheet 4 is formed of laminated sheeting composed of a finely porous resin film 4a and nonwoven fabric 4b, and the fastening member 6 is formed of a male sheet member of a mechanical fastener and designed to be brought into direct contact with the surface of the nonwoven fabric 4b constituting the back sheet 4 to fasten the disposable diaper 1.

In greater detail, the back sheet 4 should be permeable to moisture and leakproof against liquid. In order to satisfy both requirements of tear strength and texture, it is preferable to provide the nonwoven fabric 4b as a surface layer so that the fastening member 6 may be stuck to any part of the back sheet 4.

Specifically the back sheet 4 can have the structure shown in FIG. 6(a), in which a single finely porous resin film 4a and a single nonwoven fabric 4b are laminated one on another, or the structure shown in FIG. 6(b), in which nonwoven fabric 4b is laminated on both sides of a finely porous resin film 4, and the like. It is necessary that the finely porous resin film 4a in the structure of FIG. 6(a) be on the side facing the absorbent member 3 with the nonwoven fabric 4b on the surface side of the back sheet 4.

The finely porous resin film 4a and the nonwoven fabric 4b are laminated one on another through partial adhesion as shown in FIG. 7. If they are adhered all over the lamination plane, the moisture permeability would be reduced or completely lost, and the back sheet will have increased flexural rigidity, sometimes feeling stiff and having extremely poor texture. Therefore, partial adhesion as in this embodiment is preferred.

As shown in FIGS. 4 through 8, the adhesion pattern between the finely porous resin film 4a and the nonwoven fabric 4b is a continuous linear pattern 10 which provides continuous linear adhesive areas 4c in high-strength areas comprising a waist area 7 located at the waist of a wearer, leg areas 8 located at each leg of a wearer, and a landing area 9 with which the fastening member 6 is to be brought into contact and a discontinuous dotted pattern which provides a large number of discontinuous dot adhesive areas 4c' in areas 10a other than the high-strength areas.

The adhesion having the linear pattern in the high-strength areas provides sufficient strength for sticking a fastening member thereto or for providing an elastic member.

As shown in FIG. 5, it is preferable that the ratio of the length $L_1$ of the waist area 7 to the total length $L_D$ of the disposable diaper ($L_1/L_D$) is 0.02 to 0.1; the ratio of the length $L_2$ of the leg area 8 to the total length $L_D$ of the disposable diaper ($L_2/L_D$) is 0.02 to 0.1; and the ratio of the length $L_3$ of the landing area 9 to the total length $L_D$ of the diaper ($L_3/L_D$) is 0.05 to 0.25.

While there are cases as follows, depending on the process for producing the back sheet, in which the dot adhesive areas are also formed in the above-described high-strength areas, all the areas where the above-described linear adhesive area is formed correspond to the above-identified high-strength areas in the present invention.

Taking the fastening strength at the fastening member, operating simplicity in fastening, and softness into consideration, linear patterns made up of a cluster of hexagons, diamonds, triangles, circles, etc. or mixed patterns composed of two or more of these shapes are preferred. In this particular embodiment a pattern made up of a cluster of hexagons is used as shown in FIG. 7. In this invention, the pattern composed of hexagons or the mixed pattern are preferred from the standpoint of tensile and tear strength of the sheet, fastening performance of the fastening member, and the texture.

The dotted pattern is designed to improve the texture. It is preferred for tear strength and texture that the dot adhesive areas be arranged in the oblique direction with reference to the width direction of the sheet as illustrated in FIG. 7 rather than arranged in parallel or perpendicularly to the width direction. While not limiting, the individual dot adhesive areas preferably have a circular shape, a diamond shape, a hexagonal shape, etc. from the viewpoint of texture.

The linear adhesive area 4c in the linear pattern preferably has a line width of 0.2 to 3 mm, particularly 0.5 to 1.5 mm. The area ratio of the adhesive area (the area where the linear adhesive areas 4c are formed) to the non-adhesive area (the area where neither the linear adhesive area 4c nor the dot adhesive area 4c' is formed) in each high-strength area (the area of the adhesive area: the area of the non-adhesive area) preferably ranges from 5:95 to 70:30, particularly 20:80 to 40:60. If the line width is less than 0.2 mm, the adhesive force is insufficient. If it exceeds 3 mm, the softness is reduced. If the area ratio of the adhesive area is less than 5, the laminated sheet has insufficient shape retention. If it exceeds 70, the adhesive area increases, but the texture deteriorates. The moisture permeability is also reduced in some cases. Therefore, the above-specified area ratio is preferred.

The area of the individual dot adhesive areas 4c' in the dotted pattern is preferably 0.05 to 5 $mm^2$, particularly 0.5 to 2 $mm^2$. The area ratio of the adhesive area (the area where the dot adhesive areas 4c' are formed) to the non-adhesive area (the area where no dot adhesive area 4c' is formed) in each area 10a other than the high-strength areas (the area of the adhesive area: the area of the non-adhesive area) preferably ranges from 1:99 to 40:60, preferably 5:95 to 20:80. If the area of each dot adhesive area is less than 0.05 mm$^2$, it is difficult to secure adhesion. If it exceeds 5 mm$^2$, the adhesive area becomes harder and larger, deteriorating the texture. If the area ratio of the dot adhesive is less than 1, the adhesive force of the laminated sheet is insufficient. If it exceeds 40, the texture deteriorates.

While the finely porous resin film 4a and the nonwoven fabric 4b can be adhered to each other in a usual manner by means, e.g., of an adhesive or a hot-melt adhesive, it is preferable that they are adhered by heat fusing in view of productivity, safety, and economy and also for avoiding reduction in sheet softness to keep a good texture.

The method of heat fusing is not particularly restricted, and generally employed methods, such as a hot roll method, a radio frequency method, and an ultrasonication method, are used. A hot roll method is particularly preferred in view of productivity.

Heat fusing of the high-strength areas and that of the other areas 10a may be carried out simultaneously. However, considering that positioning must be done on the production line, it is preferable that the laminate is heat-fused in dot patterns over the entire area and then heat-fused in a line pattern on the portions corresponding to the high-strength areas where dot adhesive areas have already been formed, thereby providing the high-strength areas and, at the same time, the other areas 10a. That is, the above-mentioned two-stage hot fusing allows adopting a method in which the dotted pattern is made off-line of the production of absorbent articles and the linear pattern is made in-line.

Where the linear pattern formed overlaps the previously provided dotted pattern, the area ratio of the adhesive area (the area where the linear adhesive areas 4c or the dot adhesive areas 4c' are formed) to the non-adhesive area (the area where neither the linear adhesive area 4c nor the dot adhesive area 4c' is formed) (i.e., the area of the adhesive area: the area of the non-adhesive area) preferably ranges from 10:90 to 80:20, particularly 20:80 to 50:50.

In forming the areas 10a other than the high-strength areas by heat fusing to give good adhesion in dots at the laminating interface between the finely porous resin film 4a and the nonwoven fabric 4b, the laminated sheet is preferably heated from the side of the finely porous resin film. In forming the high-strength areas, on the other hand, heating of the laminated sheet for giving linear adhesive areas is preferably done from its nonwoven fabric side so as not to impair the function as a female sheet member of a mechanical fastener.

The areas 10a other than the high-strength areas preferably have a moisture permeability of not lower than 0.8 g/[100 cm$^2$·hr], particularly 1.0 to 3.0 g/[100 cm$^2$·hr], and a leakproofness of not less than 30 minutes, still preferably not less than 60 minutes, particularly preferably not less than 120 minutes, as measured against artificial urine having a surface tension of 45 dyne/cm at a liquid pressure of 35 gf/cm$^2$.

The back sheet 4 preferably has an apparent thickness (the same as that for the nonwoven fabric 4b) of 20 to 700 μm, particularly 30 to 400 μm.

Where the adhesive areas of the back sheet 4 are provided at intervals greater than 2 cm$^2$, the thickness at the non-adhered thick area was taken as an apparent thickness.

Figure 9A:
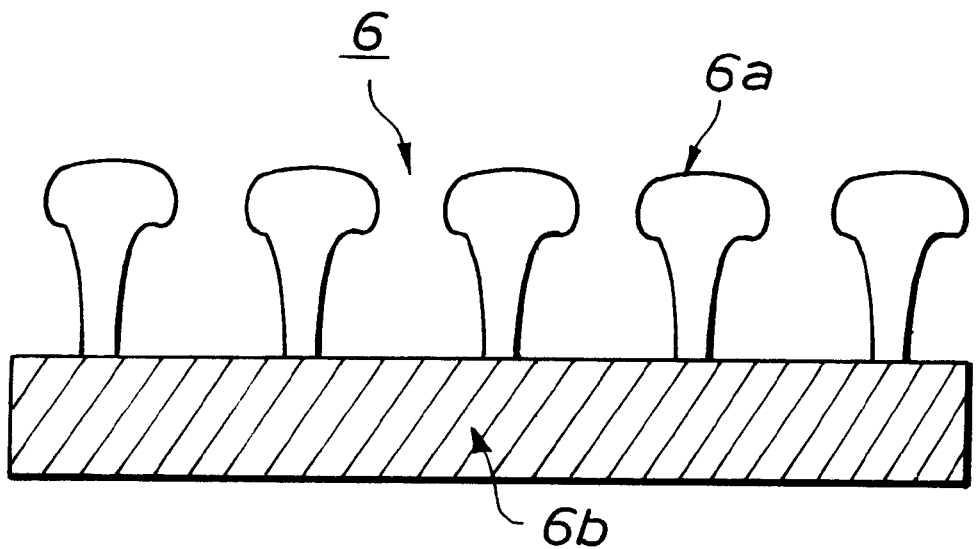
FIGS. 9(a) and 9(b) each schematically show an enlarged cross-sectional view of the male sheet member of a mechanical fastener.
Figure 9B:
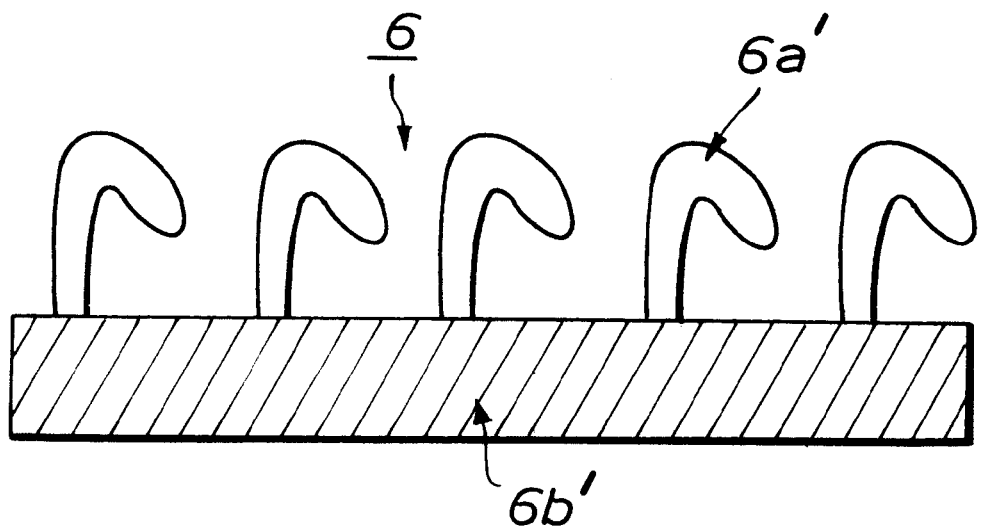

The male sheet member of the mechanical fastener which can be used to form the fastening member 6 includes the sheets shown in FIGS. 9(a) and (b).

The male sheet member shown in FIG. 9(a) comprises a base sheet 6b having provided thereon a large number of anchor-shaped male engaging pieces 6a. The male sheet member shown in FIG. 9(b) comprises a base sheet 6b' having provided thereon a large number of hook-shaped male engaging pieces 6a'.

The male engaging pieces 6a or 6a' and the base sheet 6b or 6b' are not particularly limited in material, but are preferably made up of thermoplastic resins based on productive and economical considerations. Suitable examples of useful thermoplastic resins are polyethylene, polypropylene, polyamide, and polyester, etc. The material of the male engaging pieces 6a or 6a' and that of the base sheet 6b or 6b' may be the same or different. The male engaging pieces 6a or 6a' and the base sheet 6b or 6b' may be formed by integral molding, or they may be formed separately and then adhered. From the productive and economical considerations, integrally molded male sheet members are preferred.

The density of the male engaging pieces is preferably 25 to 250 pieces per cm$^2$.

The male sheet member is attached to each side edge of the rear waist body portion with its side having no male engaging pieces fixed thereto via an adhesive or through heat fusing, thereby providing the fastening member.

It should be understood that the absorbent articles according to the present invention are not construed as being limited to the aforementioned particular embodiment, and various changes and modifications can be made without departing from the spirit and scope of the invention. For instance, the landing area does not need to have a clear borderline. The borderline between an area having the linear pattern (i.e., high-strength area) and other areas having the dotted pattern can rather be made ambiguous so that the change from the linear pattern to the dotted pattern may occur with gradation. In this case, the stress from the fastening member toward the back sheet is diffused to make a better fit.

As long as the above-described function is fulfilled, the male sheet member of the mechanical fastener is not limited in shape and the like, and any kind of generally known mechanical fasteners (for example, MAGIC TAPE) can be made use of, irrespective of whatever the disclosed technique is called.

The invention will now be illustrated in greater detail with reference to examples, but the invention is by no means limited thereto.

EXAMPLE 1

A finely porous polypropylene resin film as a finely porous resin film was prepared as follows.

A polypropylene resin (a homopolymer produced by Chisso Corp.; melt index: 0.4; melting point: 169° C.) was extruded and blown into a tubular film having a thickness of 25 μm from a 50 mm single-screw extruder (L/D=28) equipped with a circular die having a die lip clearance of 1 mm and a die lip diameter of 200 mm under conditions of 250° C., a draft ratio of 40, and a blow-up ratio of 1.0. The tubular blown film was cut and opened and taken up to obtain a film.

The resulting film was subjected to a heat treatment in an oven at 100° C. for 2 hours.

The heated film was stretched at a stretch ratio of 2.0 and a film feed rate of 2 m/min, followed by heat-treatment to cause 25% shrinkage (heat set) by means of stretching equipment having a working width of 1500 mm and comprised of two preheating rolls having a diameter of 500 mm, two stretching rolls having a diameter of 100 mm, two heat-treating rolls having a diameter of 500 mm, and two cooling rolls having a diameter of 500 mm, to give a finely porous polypropylene resin film. The surface temperature of the preheating rolls, stretching rolls, heat-treating rolls, and cooling rolls was set at 50° C., 50° C., 120° C., and 27° C., respectively.

The resulting finely porous polypropylene resin film showed uniform whitening and had a thickness of 21 to 22 μm.

Nonwoven fabric was prepared as follows.

Conjugated filaments comprising polypropylene having a melting point of 161° C. as a core and low melting point polypropylene having a melting point of 148° C. as a sheath at a cross-sectional core to sheath area ratio of 60/40 and having a thickness of 2 denier were prepared. The conjugated filaments were cut to 38 mm lengths, formed into a web having a basis weight of 22 g/m² by means of a carding machine, and then passed under a heat roll to give nonwoven fabric having an apparent thickness of 290 μm.

The resulting finely porous polypropylene resin film 4a and nonwoven fabric 4b was combined into a back sheet 4 shown in FIG. 6(a). That is, the finely porous polypropylene resin film 4a and the nonwoven fabric 4b were each slit to 350 mm width and laminated one on another. The laminate was passed through a partial heat sealer composed of an embossing roll and a back-up roll both having a diameter of 100 mm and a working width of 600 mm with the finely porous polypropylene resin film 4a facing the embossing roll, to form dot adhesive areas 4c'. The embossing roll used was dotted with column-shaped projections having a diameter of 1 mm and a height of 0.5 mm at intervals of 2 mm, the projections being arranged in the oblique direction (at an angle of 45°) with reference to the revolving direction of the roll. The embossing was carried out at an embossing roll surface temperature of 154° C., a linear pressure of 33 kg/cm onto the back-up roll (paper roll), and a laminate feed rate of 30 m/min. The resulting laminated sheet had an apparent thickness of 300 μm and an area ratio of adhesive area/non-adhesive area of 20/80.

The sheet having dot adhesive areas formed was then passed through a partial heat sealer comprised of an embossing roll and a back-up roll both having a diameter of 160 mm and a working width of 600 mm with the nonwoven fabric 4b facing the embossing roll. The embossing roll used here was an iron-made roll having its surface area of 60 mm in the revolving direction of the roll and 220 mm in roll width direction engraved with a positive pattern comprising a cluster of hexagons each side of which had a line width of 1 mm and a length of 5 mm. The embossing was carried out at an embossing roll surface temperature of 154° C., a linear pressure of 33 kg/cm onto the back-up roll (paper roll), and a laminate feed rate of 30 m/min to give continuous sheeting for a back sheet having linear adhesive areas 4c formed at a prescribed position. The resulting continuous sheeting for a back sheet had linear adhesive areas 4c for every 500 millimeters in the MD direction to provide the landing area 9. The waist area and the leg areas were also formed in the respective prescribed positions. The individual landing area 9 had a width of 60 mm in the MD direction and a length of 220 mm, centered in the CD direction. The landing area 9 had an apparent thickness of 280 μm and an area ratio of adhesive area to the non-adhesive area was 22/78.

The area ratio of the adhesive area inclusive of the previously formed dot adhesive areas to the non-adhesive area was about 38/62.

The thus obtained back sheet was evaluated for moisture permeability, leakproofness, tear strength, and texture as follows. As a result, the back sheet had a moisture permeability of 1.6 g/[100 cm²·hr] in the areas other than the high-strength areas (the areas where only dot adhesive areas are formed), a leakproofness of more than 180 minutes, a tear strength of greater than 700 gf/mm, and a texture graded "A".

Method of Evaluation (1) Moisture Permeability:

Measured in accordance with JIS Z0208.

(2) Leakproofness:

The sheet was fixed over one end of a cylinder having a diameter of 3 cm with a ring having silicone rubber packing to make a sheet stopper having a diameter of 3 cm. Artificial urine was put in the cylinder to a height of 35 cm. The time for the liquid to start leaking through the sheet stopper was measured. The artificial urine comprised 1.94 wt % of urea, 0.795 wt% of sodium chloride, 0.110 wt % of magnesium sulfate, 0.062 wt % of calcium chloride, 0.197 wt % of potassium sulfate, and 0.010 wt % of red #2 (dye) and had a surface tension adjusted to 45 dyne/cm with polyoxyethylene nonyl phenyl ether.

(3) Tear Strength:

A specimen having a width of 30 mm and a length of 60 mm in the stretching direction (MD direction) was prepared. A notch 30 mm in length was made from the middle of one longitudinal end of the specimen toward the center. Each of the two ends thus split was fitted to a tensile tester, one with its surface up, and the other down. The specimen was torn at a rate of pulling of 300 mm/min to obtain an average stress.

(4) Texture:

The texture of the back sheet was evaluated by touch and graded as follows.

A . . . Soft and very satisfactory in texture.

B . . . Soft and satisfactory in texture.

C . . . Slightly hard and slightly poor in texture.

D . . . Hard and poor in texture.

A disposable diaper shown in FIG. 4 was prepared as an absorbent article of the invention by using the above-described back sheet (300 mm wide, 500 mm long) and the above-described male sheet member of a mechanical fastener (20 mm×20 mm). A nonwoven fabric sheet generally used in common disposable diapers was used as a topsheet 2, and a sheet of multiple piles of mixed fibers of pulp and an absorbent polymer, which is generally used in common disposable diapers, was used as an absorbent member 3.

The male sheet member of a mechanical fastener used here was MECHANICAL FASTENER HOOK CS-200 (900PPI) produced by Minnesota Mining & Mfg. Co. (3M) and available from Sumitomo 3M Ltd., which has about 120 anchor shaped projections per cm² on its base sheet and an adhesive on the back side of the base sheet.

As compared with diapers prepared by using a conventional back sheet and a fastening tape, the resulting disposable diaper suffered no leakage of urine, could be fastened satisfactorily even after repetition of fastening and unfastening, and provided a good fit and an excellent texture.

EXAMPLE 2

A disposable diaper was prepared in the same manner as in Example 1, except for using nonwoven fabric A' described below.

The nonwoven fabric A' used was tested in accordance with the following test methods. As a result, the tack and the peeling strength were 83 gf and 160 gf, respectively, and the fluffing was graded 2.

As compared with diapers prepared by using a conventional back sheet and a fastening tape, the resulting disposable diaper suffered no leakage of urine, could be fastened satisfactorily even after repetition of fastening and unfastening, and provided a good fit and an excellent texture.

Nonwoven Fabric A'

Nonwoven fabric A' was prepared by using the following mixing percentages by weight of fibers A and B in accordance with the process described below.

Fibers A: Fibers having a core/sheath structure comprising polyethylene terephthalate (PET) as a core and polyethylene (PE) as a sheath at a core/sheath weight ratio of 40/60; fiber size: 4 denier×51 mm; the mixing percentage of fibers A: 50 wt %.

Fiber B: Fibers having a core/sheath structure comprising PET as a core and polypropylene (PP) as a sheath at a core/sheath weight ratio of 50/50; fiber size: 4 denier×51 mm; the mixing percentage of fibers B: 50 wt %.

Process: Fibers A and B were mixed at a mixing ratio of 50/50 by weight and made into a card web. The resulting card web was heat treated with hot air at a flow of 1 to 2 m/sec for 6 seconds to obtain nonwoven fabric A' having a basis weight of 27 g/m$^2$.

The resulting nonwoven fabric was tested according to the following test methods. As a result, the tack, the peeling strength, and the tear strength were 83 gf, 160 gf and 2160 gf, respectively, and the fluffing was graded 2.

(Tack)

Figure 10:
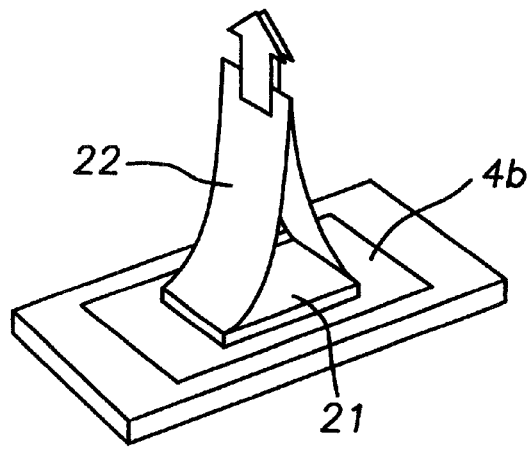
FIG. 10 shows a method for measuring a tack.

As shown in the FIG. 10, a male member 20 (30×30 mm, see FIG. 11) (CS-200 900PPI, produced by 3M) was pressed onto a piece of the resulting nonwoven fabric 4b by applying a static load of 16.7 gf/cm$^2$ for 10 seconds, and a base strip 22 having thereon the male member 20 was pulled up at a speed of 300 mm/min in the direction shown by the arrow. The pulling force at the release of the male member 20 from the nonwoven fabric 4b was measured as a tack.

Figure 11:
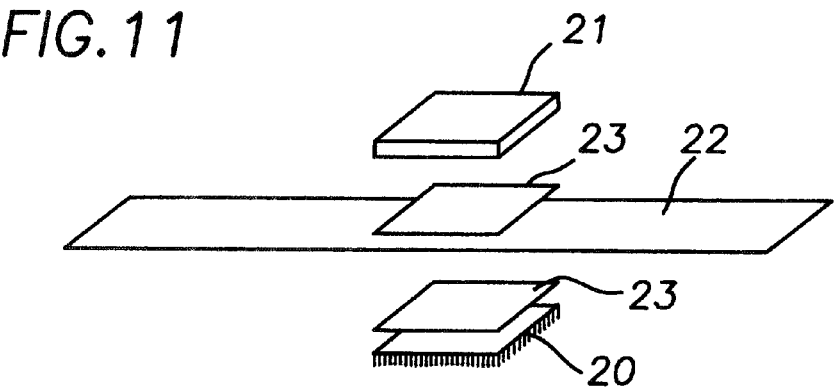
FIG. 11 shows a manner of preparing a male member sample used in the measurement of a tack.

As shown in FIG. 11, the male member 20 was fixed to one side of the base strip 22 via a double-sided adhesive tape 23. Onto the other side of the strip at the position corresponding to the male member 20 was fixed an acrylic resin plate 21 via a double-sided adhesive tape 23 so as to maintain the angle of peeling at 0°.

Figure 12:
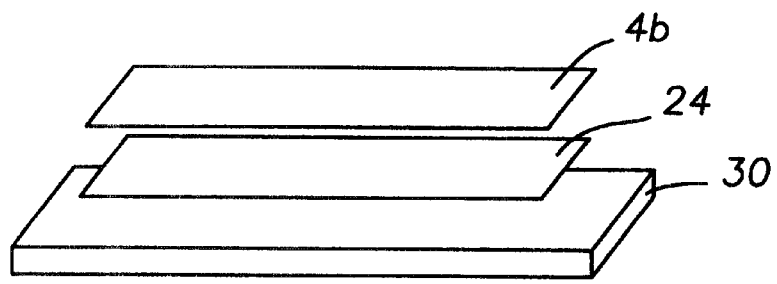
FIG. 12 shows a manner for fixing a nonwoven fabric sample used in the measurement of a tack.

As shown in the FIG. 12, the nonwoven fabric 4b was fixed on an acrylic resin plate 30 via a double-sided adhesive tape 24.

(Peeling strength)

The nonwoven fabric 4b was cut to a size of 5 cm×5 cm and stuck to the outer nonwoven fabric (back sheet) of MERRIES PANTS (a disposable diaper produced by Kao Corp.) via a double-sided adhesive tape. A 3 cm×3 cm piece was cut out of a male sheet member of a mechanical fastener. A base sheet of 3 cm×3 cm was adhered to the back side of the cut piece of the male sheet member in such a manner that a width of 10 mm from one end of the base sheet remained free (20a in FIG. 13), and a base film of the same size as the male sheet member was adhered to the base sheet to prepare a male sheet member sample 20'.

Figure 13:
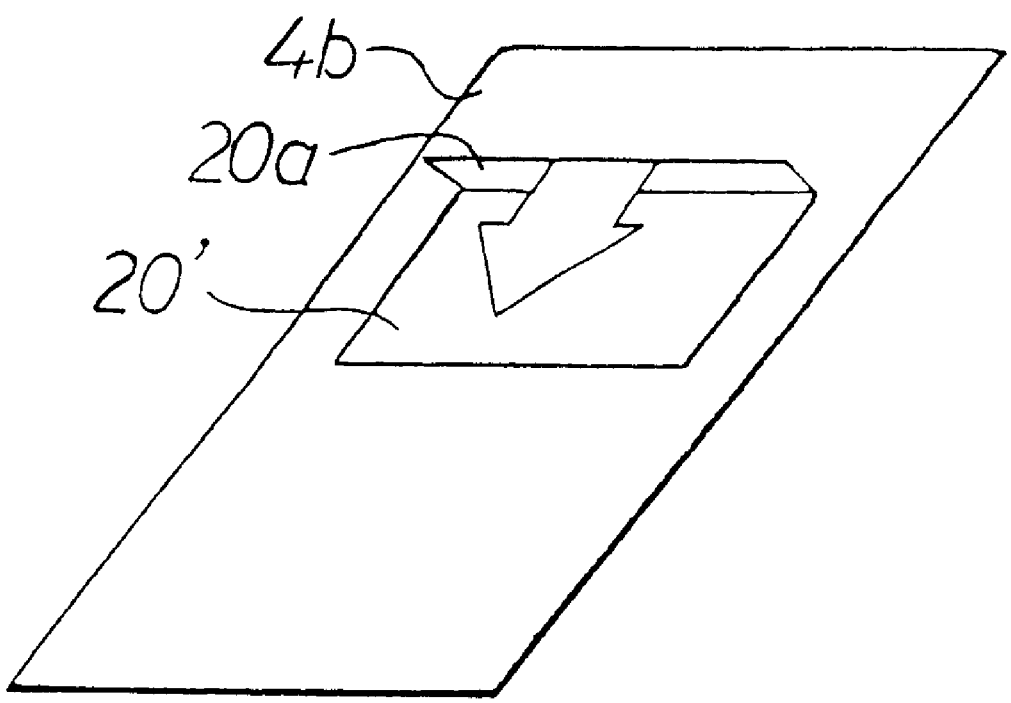
FIG. 13 shows a method for measuring a peeling strength.

As shown in FIG. 13, the male sheet member sample 20' was placed on the nonwoven fabric 4b with its 10 mm wide end (the portion consisting solely of the base sheet) free, and a double stroke of a roller weighing 1 kg was given to the male sheet member sample 20'. The male sheet member sample 20' was then peeled by pulling the end 20a to the direction (longitudinal direction of the male sheet member sample 20') indicated by the arrow at a pulling speed of 300 mm/min, and the force required for stripping the male sheet member sample 20' off the nonwoven fabric 4b was measured. The peeling test was repeated 10 times to obtain an average peeling strength. Alternatively, the measurement data were processed by peeling test mode data processing software MP-100P (MS-DOS) Ver. 43.1, produced by Orientec K.K., and the peeling strength was evaluated by the 5-point average load.

The base sheet and the base film used above are not limited in materials as far as the male member can be fixed thereon.

(Fluffing)

The surface condition of the nonwoven fabric 4b after the measurement of peeling strength was observed with the naked eye, and the fluffing was evaluated in 5 grades.

1 . . . No fluffing
2 . . . Slight fluffing
3 . . . Medium fluffing
4 . . . Considerable fluffing
5 . . . Failure of the nonwoven fabric

EXAMPLE 3

A disposable diaper was prepared in the same manner as in Example 1, except for using nonwoven fabric B' described below.

The nonwoven fabric B' was tested in the same manner as in Example 2. As a result, the tack and the peeling strength were 86 gf and 120 gf, respectively, and the fluffing was graded 1.

As compared with diapers prepared by using a conventional back sheet and a fastening tape, the resulting disposable diaper suffered no leakage of urine, could be fastened satisfactory even after repetition of fastening and unfastening, and provided a good fit and an excellent texture.

Nonwoven Fabric B'

Heat-fusible conjugated fibers 100 wt % having low heat shrinkability and high fused point strength which comprised PP having a melting point of 162° C. as a core and PP having a melting point of 143° C. as a sheath at a core/sheath weight ratio of 60/40 and had a fiber thickness of 4 denier and a fiber length of 51 mm were made into a web. The resulting web was heat treated with hot air of 146° C. for 30 seconds to obtain nonwoven fabric B' having a basis weight of 40 g/m$^2$.

Industrial Applicability

The absorbent article according to the invention has a good fit on a wearer, exhibits excellent leakproofness and breathability causing no rash while worn, and has an excellent texture.

More specifically the back sheet used in the absorbent article of the invention has moisture permeability, high strength, excellent leakproofness against low-surface tension liquids, such as urine, has a satisfactory texture, and can be fastened and unfastened repeatedly. Even though a fastening member is stuck to the back sheet at a position other than a landing area, the back sheet is not broken on unfastening followed by re-fastening. The back sheet of the invention can be manufactured by heat fusing, offering an advantage of productivity.

Since the back sheet is a laminated sheet composed of a finely porous resin film and nonwoven fabric, it is permeable to moisture and yet leakproof against liquid, has high tensile and tear strength, and feels soft on its surface with a reduced contact area with the skin. Because the nonwoven fabric serves as a female member of a mechanical fastener, a fastening member formed of a male sheet member of a mechanical fastener can be stuck anywhere, so that the diaper can be just fitted on a wearer's body without tightening up. Even if the back sheet is made relatively thin, the diaper could be fastened firmly with a good fit and easily unfastened and re-fastened without requiring any special reinforcement.

Accordingly, the absorbent article according to the invention has a back sheet that is soft and yet is not broken with no special reinforcement and also exhibits high moisture permeability while having leakproofness against liquid, and possesses a fastening function that allows unfastening followed by re-fastening. In addition, the absorbent article has soft surfaces coming into contact with the skin (corresponding, in the case of an absorbent article, to the sides of the topsheet and the back sheet that are opposite to the sides contacting the absorbent member) and has a function of minimizing the contact area with the skin.

What is claimed is:

1. An absorbent article which comprises a liquid permeable topsheet, a liquid impermeable back sheet, and an absorbent member interposed between said topsheet and said back sheet, which article substantially forms a rectangular shape, and, while worn, forms a front waist body portion located at a front waist of a wearer and a rear waist body portion located at a rear waist of the wearer, said rear waist body portion having at each side thereof a fastening member for fastening the absorbent article, and wherein:

said back sheet is made up of laminated sheeting composed of a finely porous resin film and a nonwoven fabric mounted exteriorly of the film;

each of said fastening members is formed of a male sheet member of a mechanical fastener and is designed to be brought into direct contact with said nonwoven fabric of said back sheet in said front waist body portion wherein said nonwoven fabric in said front waist body portion with which each of said fastening members is brought into direct contact when fastened defines a landing area;

said finely porous resin film and said nonwoven fabric are laminated one on another with partial adhesion, the partial adhesion between said finely porous resin film and said nonwoven fabric having (i) a continuous linear pattern which provides continuous linear adhesive areas of high-strength in a waist area locatable at a waist of the wearer, leg areas locatable at legs of the wearer, respectively, and said landing area with which each of said fastening members is brought into contact with when fastened, and (ii) a discontinuous dotted pattern which provides a large number of discontinuous dot adhesive areas in areas other than said high-strength areas.

2. The absorbent article according to claim 1, wherein said linear adhesive areas have a line width of 0.2 to 3 mm, an area ratio of adhesive areas to non-adhesive areas in said waist area and said leg areas having ratio values from 5:95 to 70:30, each discontinuous dot adhesive area being in a range from 0.05 to 5 $mm^2$, and an area ratio of the adhesive areas to the non-adhesive areas in said discontinuous dot adhesive areas having ratio values from 1:99 to 40:60.

3. The absorbent article according to claim 1, wherein said finely porous resin film is made of a crystalline polyolefin resin, and said nonwoven fabric is made of a polyolefin series of filaments.

4. The absorbent article according to claim 1, wherein said nonwoven fabric is made of a mixture of at least two kinds of heat-fusible fibers which are hardly fused together, in which fibers of one kind being strongly fused at intersections, and the intersections are distributed throughout the nonwoven fabric.

5. The absorbent article according to claim 1, wherein said nonwoven fabric is made of fibers containing at least 50% by weight of heat-fusible conjugated fibers having a core and sheath, each core and each sheath are made of the same type of resinous components, each sheath has a first melting point, each core has a second melting point, said first melting point is lower than said second melting point.

6. The absorbent article according to claim 1, wherein said finely porous resin film and said nonwoven fabric are laminated by heat fusion.

7. The absorbent article according to claim 1, wherein said dot adhesive areas have a moisture permeability of not less than 0.8 g/100 $cm^2$·hr.

* * * * *